(12) United States Patent
Sonstein

(10) Patent No.: US 8,535,328 B2
(45) Date of Patent: Sep. 17, 2013

(54) MEDICAL DEVICE INSERTION INSTRUMENT

(75) Inventor: William J. Sonstein, Old Westbury, NY (US)

(73) Assignee: Neurological Surgery PC, Rockville Centre, NY (US)

( * ) Notice: Subject to any disclaimer, the term of this patent is extended or adjusted under 35 U.S.C. 154(b) by 137 days.

(21) Appl. No.: 12/925,092

(22) Filed: Oct. 12, 2010

(65) Prior Publication Data
US 2012/0089149 A1  Apr. 12, 2012

(51) Int. Cl.
*A61B 17/56* (2006.01)
*A61B 17/60* (2006.01)
*A61F 2/00* (2006.01)

(52) U.S. Cl.
USPC ............................................ 606/100; 606/99

(58) Field of Classification Search
USPC .............. 606/99, 100, 86 A, 86 B, 86 R, 914; 81/28, 463–466
See application file for complete search history.

(56) References Cited

U.S. PATENT DOCUMENTS 5,190,549 A * 3/1993 Miller et al. ..................... 606/85
6,712,819 B2 * 3/2004 Zucherman et al. ........ 606/86 A

* cited by examiner

*Primary Examiner* — Andrew Yang
*Assistant Examiner* — Diana S Jones
(74) *Attorney, Agent, or Firm* — Abelman, Frayne & Schwab

(57) ABSTRACT

A known x-stop implantation instrument is modified to provide a slide hammer mechanism to selectively apply an impact force. Both the axial location of the slide hammer and the angle of the slide hammer may be adjusted. A surgeon, when necessary or desirable, may thus apply an impact force to the forward end of the implement having a least a component of force in the direction of insertion of the x-stop device. The invention permits the surgeon to vary both the position along the shaft where the impact is applied as well as the angle at which the impact is applied relative to the direction of insertion.

2 Claims, 4 Drawing Sheets

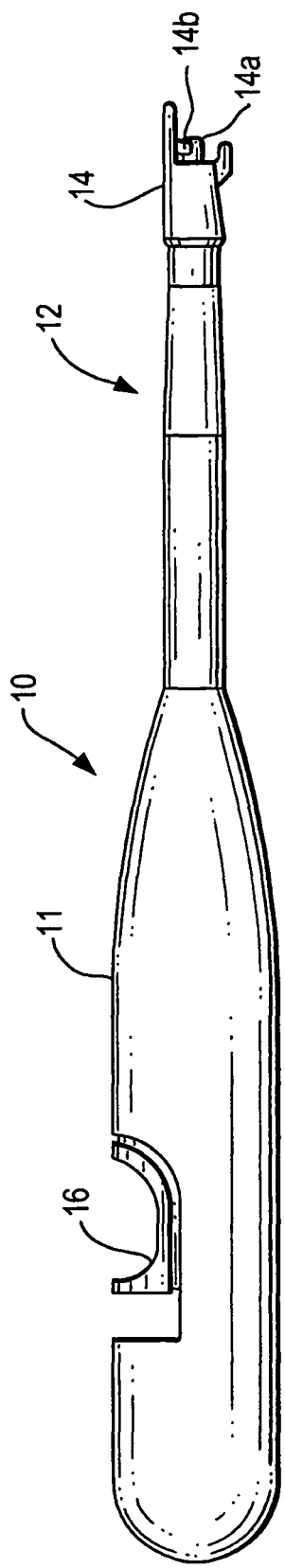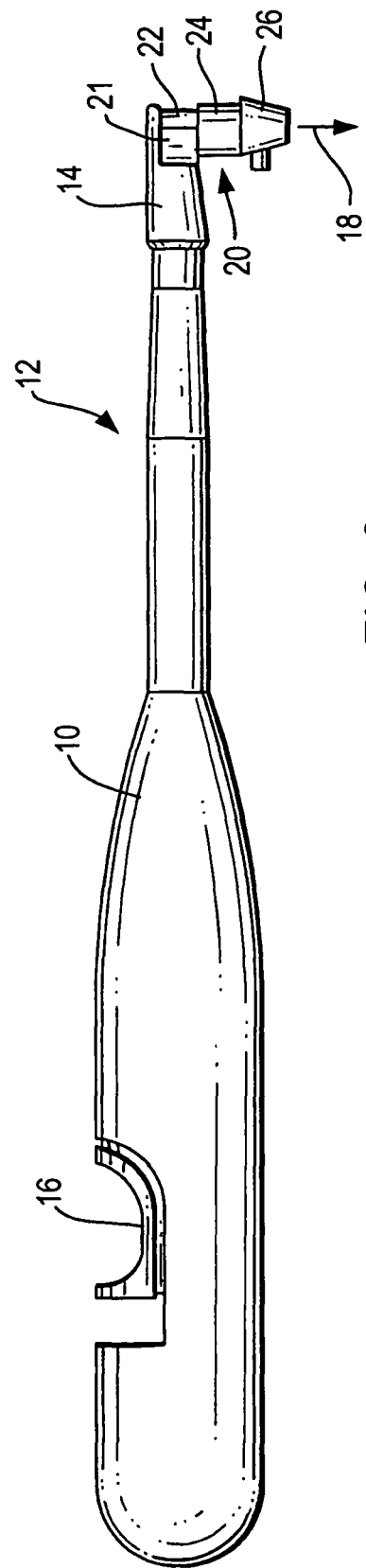
FIG. 1
Prior Art
FIG. 2
Prior Art

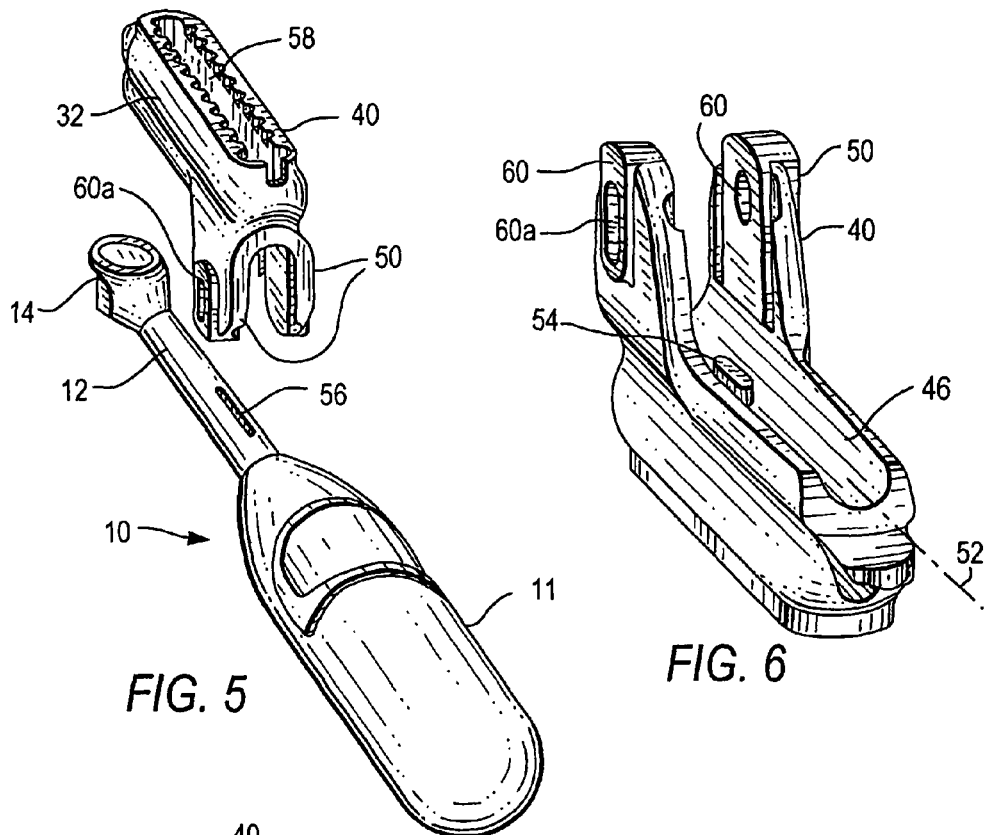
FIG. 5
FIG. 6
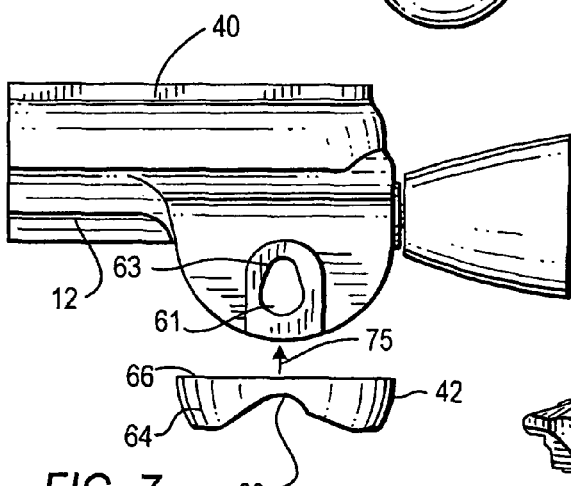
FIG. 7
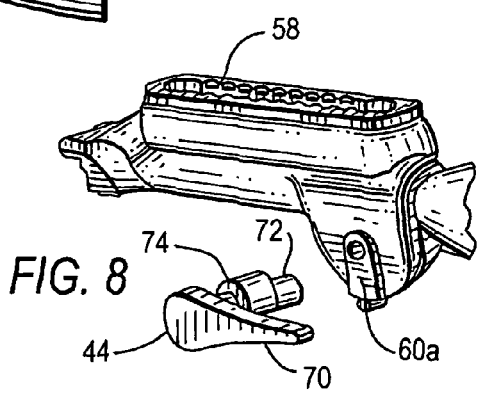
FIG. 8

MEDICAL DEVICE INSERTION INSTRUMENT

BACKGROUND OF THE INVENTION

Lumbar spinal stenosis is a condition in which the nerves in the spinal canal become compressed. Patients with spinal stenosis can suffer from pain in the lower back and legs. The pain is classically worse when patients walk, and better when they stop walking and flex forward. This is because flexion tends to open up the spinal canal.

As an alternative to traditional laminectomy, there is a small titanium implant device available known as "x-stop" which may be placed between the posterior spinous processes of the affected levels (usually L3/4 or L4/5). Implanting the x-stop device effectively produces a permanent slight flexion, which in turn can provide symptom relief and improve physical function. The x-stop may be implanted with minimally invasive surgery; there is usually no removal of tissue or bone; and the procedure is reversible if necessary.

In one known procedure, the patient is positioned in the lateral decubitus position (right side down) and anesthetized locally. A 4-8 cm midline incision is made to expose the fascia, and the surgeon then incises the fascia on either side of the spinous processes and the supraspinous ligament. A dilator and, in turn, a sizer may then be used to open up the interspinous ligament. At this point, the patient is ready for the x-stop implant.

Referring to FIGS. 1-3, a known instrument 10 for implanting the x-stop device includes a handle 11, a shaft 12, and a securement mechanism 14. The securement mechanism is mechanically coupled to a finger-operated slider 16. When the slider 16 is retracted, an axially extending rod 14a is retracted, and a pair of pins (one of which, 14b, is shown in FIG. 1) may be inserted into a pair of holes (14c, see FIG. 3) in the wings of the main portion of an x-stop device 20. When the surgeon releases the slider 16, the rod 14a moves forward into another hole 14d in the main body 21 of the x-stop device (see FIG. 3), which hole 14d is oriented at 90 degrees relative to the holes 14c, so that the securement mechanism 14 locks firmly into engagement with the x-stop device 20. The above device is described, inter alia, in U.S. Pat. No. 7,510,567, the relevant portions of which are incorporated herein by reference.

Referring to FIG. 3, the x-stop device comprises a head 21, a pair of wings 22 extending in opposite directions from the head 21, a cylindrical spacer element 24 (whose diameter may vary depending on the patient), and a wedge portion 26 with a leading edge 27.

Referring to FIGS. 2-3, when the x-stop is to be implanted, it is moved so that the leading edge 27 of the wedge portion 26 positioned between, the pair of spinous processes 28a, 28b of the affected levels. The surgeon maneuvers the handle 11 so that the wedge portion 26 moves in the direction of arrow 18 between the spinous processes 28a, 28b. Thereafter, as shown in FIG. 3, after the wedge portion 28 has passed between the spinous processes, the wings 22 position the x-stop so that the spacer element 24 is positioned between the spinous processes 28a, 28b. At this point, the surgeon again retracts the slider 16, which retracts the extending rod 14a to allow the pins 14b of the insertion instrument to be withdrawn from the holes 14c and thus allows the instrument to release the x-stop device inside the patient and withdraw the instrument.

Finally, a second wing element (not shown, but which is similar to the portions 21-22 of the main x-stop device), is inserted into the patient and secured to on the wedge portion 26, using hole 30, so that the spacer is secured on both sides of the spinous processes 28a, 28b.

SUMMARY OF THE INVENTION

The present invention is an improvement in the x-stop implant device shown and described in connection with FIGS. 1-3. More particularly, the invention allows the surgeon when necessary or desirable to apply an impact force to the forward end of the implement having a least a component of force in the direction of insertion of the x-stop device, i.e., the direction 18. The invention permits the surgeon to vary both the position along the shaft where the impact is applied as well as the angle at which the impact is applied relative to the direction of insertion.

In one embodiment, the invention is a medical instrument to assist a surgeon in implanting a medical device in a human being. The instrument includes a handle, a main body coupled to the handle, and a securement mechanism coupled to the handle for selectively securing and releasing a medically implantable device, such as an x-stop device. A slide hammer mechanism includes a slide hammer pivotably coupled to a base, and a locking mechanism for locking the slide hammer at a desired angle and for releasing said slide hammer to change angles. The main body includes a slideway receiving the base for permitting longitudinal movement of said base relative to the main body. Finally, a second locking mechanism selectively locks the base at a desired axial position. In such a manner, a surgeon may change both the axial position of the impact surface and the angle of the impact surface relative to the shaft.

Preferably, the medical instrument is designed to secure and release an x-stop device for insertion between spinous processes of affected levels of the spine in a direction generally perpendicular to the axis of the instrument. Thus, the slide hammer can deliver an impact force in which at least a component of the force is in the direction in which the x-stop device is inserted between selected spinous processes.

In another embodiment, the invention is a method for modifying a medical instrument, such as the known x-stop insertion instrument, having a handle, a securement mechanism at an end portion for selectively securing and releasing a medically implantable device, and a shaft coupled between said handle and said end portion. Such method comprising the steps of securing a main body to said shaft, and securing the base of a slide hammer mechanism in a slideway in the main body so that the axial position of the slide hammer mechanism may be changed axially. The slide hammer mechanism is provided with a slide hammer having an impact surface which is pivotably coupled to the base. The slide hammer mechanism further comprises a locking mechanism for locking said slide hammer at a desired angle of impact and for releasing said slide hammer to change angles. The method also includes the step of coupling a second locking mechanism to the main body for selectively locking the base at a desired axial position and for releasing the base to change the axial position of said base. By carrying out such method, the surgeon is provided with an impact surface for applying force in which at least one component is in a direction perpendicular to the shaft and may change both the axial position at which such force is delivered as well as the angle of the impact surface.

BRIEF DESCRIPTION OF THE DRAWINGS

FIG. 1 is a side view of a prior art insertion instrument for implanting an x-stop device in the spine of a human being;

FIG. 2 is a side view of the instrument with an x-stop device secured thereto;

FIG. 5 is an isometric view of the instrument of FIGS. 1-2 and an embodiment of a main housing used to modify such device according to the invention;

FIG. 6 is an inverted view of the main housing of FIG. 5;

FIG. 7 is a side view of a portion of the instrument and main housing of FIG. 5 together with a cam clamping block;

FIG. 8 is an isometric view of the assembly of FIG. 7 together with a lever containing a cam for locking the main housing on the instrument;

DETAILED DESCRIPTION OF PREFERRED EMBODIMENTS OF THE INVENTION

Figure 3:
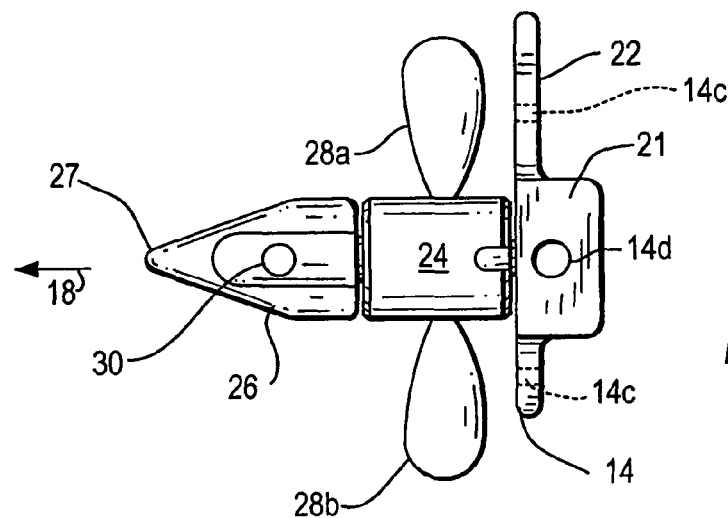
FIG. 3 is a drawing of the x-stop device after being implanted in the spine, with a pair of spinous processes shown schematically.
Figure 4:
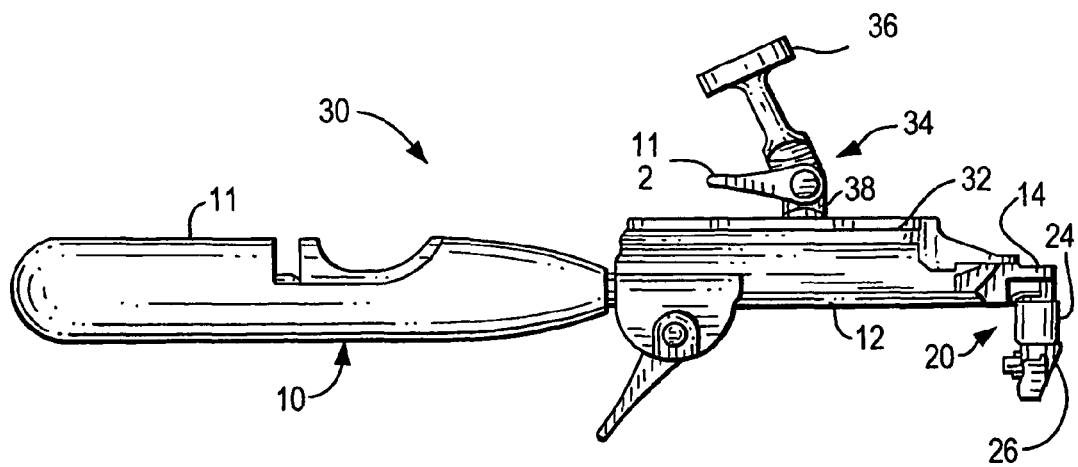
FIG. 4 is a side view of the instrument shown in FIGS. 1-2 after being modified according to the present invention.

FIG. 4 shows the overall assembly of an implement 30 according to the invention. Such implement 30 includes the known x-stop insertion tool 10 including the handle 11, shaft 12, and securement mechanism 14. A main housing assembly 32 is secured on the handle 11 as described below. The main housing assembly 32 seats a slide hammer mechanism 34 in such a manner that the mechanism 34 is axially moveable and can be locked in place at the desired axial location. Finally, the slide hammer mechanism 34 includes a slide hammer 36 which is rotatably coupled to a base 38 to allow the angle of the slide hammer 36 to be adjusted and locked.

Referring to FIGS. 5-8, the main housing assembly 32 includes a main housing 40, a cam clamping block 42, and a lever 44, each of which will be described below.

Referring to FIGS. 5-6, the main housing 40 has a generally semicircular groove 46 in its bottom surface which is generally coextensive with the shaft 12. One end of the groove 46 includes a pair of parallel flanges 50 which extend on either side of the groove 46 in a direction perpendicular to the longitudinal axis 52 of the groove 46. A locating tab 54 is formed on, or secured to, the bottom wall of the groove 46. A corresponding slot 56 is formed in the shaft 12 for seating the tab 54 so that the main housing 40 is positioned at the desired axial location and angular position.

The flanges 50 include a pair of opposed holes 60, 60a. One of the holes 60 is round. The opposite hole 60a includes a round section 61 and a second, cam-receiving section 63 (see FIG. 7) such as to have a keyhole shape. The round hole 60 and round section 61 of hole 60a are coaxial.

Finally, the upper face of the main housing 40 includes a slideway 58 which will be described later.

Referring to FIG. 7, the cam clamping block 42 includes a block portion 64 which fits between of the flanges 50. The block 42 include an upper bearing surface 66 which is preferably in the form of a groove having a radius of curvature matching the lower surface of the shaft 12 to as to be seated firmly against the shaft 12. The clamping block 42 also includes a cam surface 68 which faces away from the upper bearing surface 62.

The lever 44 includes a lever handle 70, a shaft 72, and a cam 74 formed on the shaft 72.

The sub-assembly described to this point is assembled as follow. The main housing 40 is positioned on the shaft 12 so that the locating tab 54 of the main body 40 is positioned in the groove 56 of the shaft 12. The cam clamping block 42 is then slid into the space between the flanges 50, as shown by arrow 75 in FIG. 7, until the upper bearing surface 66 is in contact with the shaft 12. Finally, referring to FIG. 8, the lever 44 is inserted into the keyhole shaped hole 60a so that the cam 74 is aligned with the cam-receiving section 63 of the hole 60a. The forward end of the shaft 72 will be received in the round hole 60. Once the cam 74 has passed completely through the hole 60a, the lever handle 70 is turned, and the cam 74 engages the cam surface 68 to secure the main body 40 to the shaft 12. At the same time, by rotating the lever portion 70 the cam 74 is no longer aligned with the cam-receiving portion 63, the lever 44 cannot be accidently withdrawn from the hole 60a.

Figure 9:
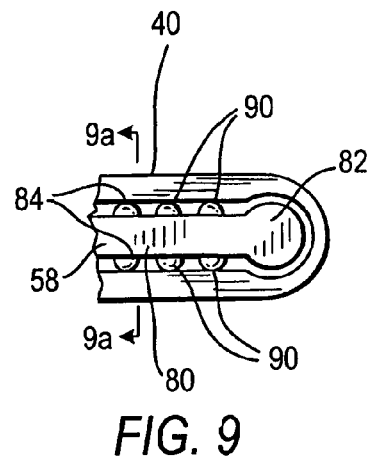
FIG. 9 is a top view of a portion of the main housing of FIG. 5.
Figure 9A:
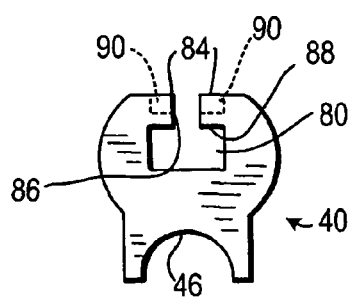
FIG. 9a is a sectional view of the main housing, taken in the direction of arrows 9a-9a of FIG. 9.

As noted above, the main body 40 has an upper surface with a slideway 58, which will now be described. As shown best in FIGS. 9 and 9a, the slideway 58 includes an axial groove 80 with an enlarged, round end 82. Except in the enlarged end 82, a pair of flanges 84 extends inwardly from the upper end of the groove 80 and are separated from one another by a longitudinal slot 86. The flanges 84 include a pair of downwardly facing bearing surfaces 88. Finally, a plurality of opposed pairs of locating holes 90 are formed in the upper surfaces of the two flanges 84.

Figure 10:
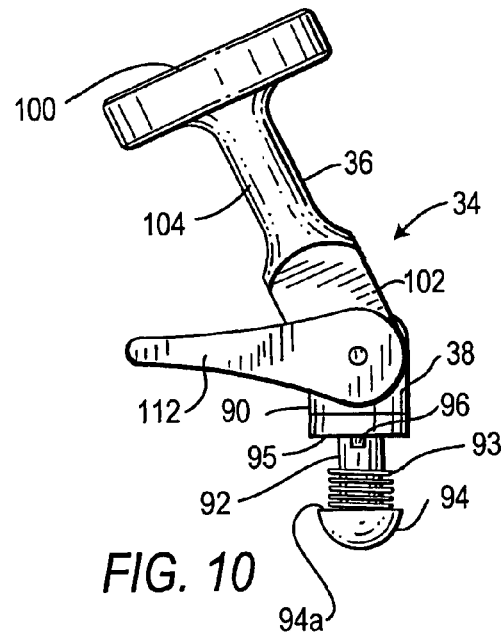
FIG. 10 is a side view of an embodiment of a slide handle assembly.
Figure 11:
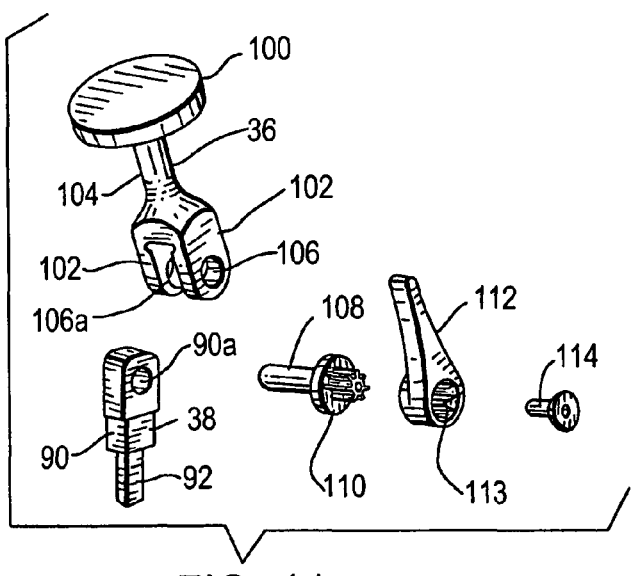
FIG. 11 is an isomeric, exploded view of various parts of the slide handle assembly.

Referring to FIGS. 10-11, the slide hammer mechanism 34 includes a base 38 having a plate portion 90 and a narrower, stem portion 92 projecting axially from a lower surface 95 of the plate portion 90. A coil spring 93 is located around the stem portion 92. A semi-spherical end cap 94, with a diameter larger than the diameter of the coil spring 93 is secured to the distal end of the stem portion 92 so that its flat surface 94a faces the lower surface 95 of the plate portion 90. The lower surface 95, which faces the cap 94, includes a pair of opposed protrusions 96 (one of which is shown in FIG. 10).

The plate portion includes a hole 91a. The slide hammer 36 includes an impact surface 100, a pair of opposed flanges 102, and a stem 104 connecting the impact surface 100 with the flanges 102. The flanges 102 include coaxial holes 106, 106a therethrough, one of which (106a) is threaded.

In order to assemble the slide hammer mechanism 34, the flanges 102 of the slide hammer 36 are disposed on either side of the base 38 so that the holes 91a, 106, 106a are aligned. A splined adaptor 110, having threads 108 at its forward end, is inserted through the unthreaded holes 106 and 91 and screwed into the threaded hole 106a. A slide hammer locking lever 112 having a splined hole 113 is positioned over the splines of the splined adapter 110, and a screw 114 is used to lock the lever 112 on the splined adapter 110. When the lever 112 is rotated in a direction to tighten the screws 108, it draws the flanges 106, 106a towards one another to lock the slide hammer at the desired angle. The mechanism can be loosened, when it is desired to change the angle of the slide hammer, by rotating the lever 112 in the opposite direction.

To complete the assembly of the insertion instrument, the now-assembled slide hammer mechanism 34 is positioned so that the cap 94 is over the enlarged portion 82 of the slideway 58. The cap 94 and spring 93 are pushed into the enlarged portion 82, and then slid axially along the slideway 58 so that the spring 93 and cap 94 are both below the flanges 84. The stem portion 92 slides in the slot 86 between the flanges 84. The lower surfaces 88 of the flanges 84 act as bearing surfaces on the spring 93, which pushes the cap 94 downwardly, which in turn will cause a pair of the protrusions 96 to enter an opposed pair of holes 90 in the slideway 58.

Referring back to FIG. 4, when a surgeon is preparing for a procedure to implant an x-stop device 20, such surgeon may set both the desired axial position of the slide hammer mechanism 34 as well as the angle of the impact surface 100 of the slide hammer 36. In order to change the axial position, the surgeon merely pulls up on the slide hammer 36. By doing so, the protrusions 96 will be pulled out of their holes 90 so that the mechanism can move axially. As soon as the desired axial position is reached, the surgeon releases the slide hammer 36 and slides the mechanism until the protrusions are aligned with a pair of holes 90, whereupon that the spring 93 pushes the protrusions 96 downwardly into the holes. The slide hammer 36 is thereby secured in the desired axial position.

To change the angle of the slide hammer 36, the surgeon merely rotates the lever 112 to allow the slide hammer to pivot, pivots the slide hammer 36 to the desired angle, and re-tightens the lever 112. Thus, the surgeon has complete freedom to determine the angle of impact as well as the position along the shaft 12 where the impact force is to be delivered.

After an operation, the instrument may be easily disassembled for cleaning sterilization, followed by reassembly prior to its next use.

The foregoing represent preferred embodiments of the invention. Variations and modifications to the exemplary embodiment will be evident to persons skilled in the art. All such variations and modifications are intended to be within the scope of the invention. Also, while the invention has been described in connection with modifying a known x-stop insertion instrument, the invention is not so limited, and is intended to be applicable to other devices.

The invention claimed is:

1. A medical instrument to assist a surgeon in implanting a medical device in a human being, said instrument having a longitudinal axis and comprising:
    a handle;
    a shaft coupled to said handle and extending in a first axial direction and having a tip end;
    a securement mechanism coupled to said tip end for selectively securing and releasing a medically implantable device;
    a main housing assembly secured to said shaft and including a slideway receiving portion which extends in said axial direction;
    a slide hammer mechanism having a base received in, and slideably movable along, said slideway in said first axial direction, said base extending in a second axial direction perpendicular to said first axial direction, a slide hammer having a hammer shaft portion extending in a third axial direction and having first and second opposite ends, an impact surface, located at said first opposite end, which is generally perpendicular to said third axial direction, said first and second axial directions lie in a common plane, wherein the second opposite end of said hammer shaft portion is pivotably coupled to said base for rotation in said plane;
    said slide hammer mechanism further comprising a first locking mechanism coupled to said shaft portion and said base for locking said hammer shaft portion at a desired angle relative to said second axial direction and for releasing said hammer shaft portion to change angles; and
    a second locking mechanism coupled to said main housing assembly for selectively locking said base at a desired axial position within said slideway and for releasing said base to change the axial position of said base, wherein said slideway is configured to allow said base, when released, to move solely in said first axial direction;
    wherein a surgeon may change both the axial position of the impact surface along the first axial direction and the angle of the impact surface relative to the first axial direction.

2. A medical instrument as defined in claim 1, wherein said securement mechanism is designed to secure and release an x-stop device for insertion between spinous processes of affected levels of the spine in a direction generally perpendicular to the axis of the instrument, wherein said slide hammer can deliver an impact force in which at least a component of the force is in the direction in which the x-stop device is inserted between selected spinous processes.

* * * * *